US009795302B2

(12) United States Patent
Rowe et al.

(10) Patent No.: US 9,795,302 B2
(45) Date of Patent: Oct. 24, 2017

(54) TISSUE ILLUMINATION SYSTEM, DEVICE, AND METHOD

(71) Applicant: Edwards Lifesciences Corporation, Irvine, CA (US)

(72) Inventors: Stanton J. Rowe, Newport Coast, CA (US); Emil Karapetian, Huntington Beach, CA (US); Erin M. Spinner, Newport Beach, CA (US); Devin H. Marr, Newport Beach, CA (US); Glen T. Rabito, San Diego, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 210 days.

(21) Appl. No.: 14/550,765

(22) Filed: Nov. 21, 2014

(65) Prior Publication Data

US 2015/0141848 A1    May 21, 2015

Related U.S. Application Data

(60) Provisional application No. 61/907,162, filed on Nov. 21, 2013.

(51) Int. Cl.
*A61B 5/00* (2006.01)
*A61B 90/30* (2016.01)

(52) U.S. Cl.
CPC ............ *A61B 5/0084* (2013.01); *A61B 90/30* (2016.02); *A61B 5/6853* (2013.01)

(58) Field of Classification Search
CPC ....... A61B 5/0084; A61B 5/0071; A61B 5/02; A61B 5/48; A61B 5/6853; A61B 90/30
See application file for complete search history.

(56) References Cited

U.S. PATENT DOCUMENTS

| 5,588,952 A | 12/1996 | Dandolu |
| 5,593,405 A * | 1/1997 | Osypka .............. A61B 1/00082 600/108 |
| 6,893,394 B2 | 5/2005 | Douglas et al. |
| 2003/0097122 A1* | 5/2003 | Ganz ...................... A61B 18/18 606/7 |
| 2008/0058650 A1* | 3/2008 | Saadat .............. A61M 25/1002 600/478 |

* cited by examiner

*Primary Examiner* — Bo J Peng
(74) *Attorney, Agent, or Firm* — Michael Crapenhoft, Esq.

(57) ABSTRACT

Implementations of the tissue illumination systems, devices, and methods disclosed herein take advantage of the translucent nature of tissue to reveal properties by light transmission, for example, tissue type, tissue transition locations, underlying structures, and the like, that are not easily distinguished by reflected light. Illuminating a back-side of a translucent tissue permits a user to distinguish between different types of tissue, tissue transition locations, and/or structures that are difficult or impossible to discern under overhead or front-side illumination. Implementations include a light source that is positionable behind a tissue or disposable within a body cavity or duct, for example, within a heart ventricle.

1 Claim, 31 Drawing Sheets

TISSUE ILLUMINATION SYSTEM, DEVICE, AND METHOD

This application claims priority to U.S. Provisional Patent Application No. 61/907,162, filed on Nov. 21, 2013, and hereby incorporated by reference in its entirety.

FIELD

The present application concerns surgical equipment, and in particular, systems for distinguishing between types of tissue during surgery.

BACKGROUND

During mitral valve repair or replacement surgery, surgeons typically use a surgical loupe, headlamp and/or standard overhead surgical lights in order to illuminate the surgical field. Illumination from these devices fails to allow the surgeon to easily distinguish between various tissue transition points and/or structures.

SUMMARY

A tissue illumination system permits a user to distinguish between different types of tissue using a lighting system that illuminates a back-side of the tissue, thereby distinguishing tissue types, tissue transition locations, and/or structures by light transmissibility. Implementations include a light source that is deployed within a body cavity or duct, for example, within a heart ventricle.

Disclosed herein are implementations of devices for illuminating a cardiac tissue from within a cardiac chamber to improve visualization. The devices may include a body and at least one light emitter supported by the body. The body and light emitter are dimensioned for placement within a cardiac chamber. The devices may also include a positioning mechanism with at least one positioning member. The member may be shaped and dimensioned for positioning the body and light emitter within the cardiac chamber so as to illuminate cardiac tissue at least partially between the viewer and the light emitter.

The at least one light emitter may include chemiluminescent sources, light emitting diodes, electroluminescent wires, solid state lasers, or fiber optic cables.

The devices may include a power source operable to generate power for the at least one light emitter.

Some implementations of the device may include a control unit operable to control a light emitted from the light emitter.

The body of the device may have a spherical shape. It may also be deformable or inflatable.

The positioning member may have an elongate shape of sufficient length and small enough diameter to be looped around and under the valve annulus, and wherein the light emitters are supported along the length of the body.

The body of the device may include at least two curved body pieces and at least one coupling mechanism configured to removably join the body pieces. The coupling mechanism may include magnets, hook-and-loop fasteners, clips, latches, or bayonet mounts.

In some implementations, the positioning member may include one or more elongate limbs coupled to, and extending from, a limb connection point located on the body. The elongate limbs include an end configured to couple to the limb connection point. The elongate limbs may also include at least two branches, and a light emitter positioned between the branches. In some implementations, the light emitters may be positioned along the length of the elongate limbs. The limbs may also include at least one adjustment feature, which may be a malleable material configured to bend. In other implementations, the adjustment feature may be a telescoping mechanism.

In some implementations, the body is inflatable. The light emitter is positioned inside the body or outside of the inflatable body. The inflatable body may have an elongate shape configured to extend around and under the valve annulus.

In some implementations, the body is sufficiently elongate and small enough in diameter to extend through a cardiac valve. The light emitter may be positioned at an illuminating end of the body, and the positioning mechanism is positioned at an end opposite the illuminating end. The positioning member may include a handle. In some implementations, the body may include a pair of forceps, and the positioning member is the end opposite the illuminating end.

In some implementations, the positioning member includes a suture line with a first end attached to the device. The suture line may include a loop. In other implementations, the positioning member may include a retrieval stick dimensioned to extend through a cardiac valve. The retrieval stick may have a retrieval stick tip that includes a hook-and-loop fastener to adhere to hook-and-loop fasteners on the body of the device. In other implementations, the retrieval stick tip may include a magnet to adhere to a magnetic material on the body of the device.

In some implementations, the power source is dimensioned for placement within the cardiac chamber. The power source may be positioned adjacent the light emitter and the body of the device. In other implementations, the power source is configured to remain outside of the cardiac chamber during its operation.

In some implementations, the control unit may include a shading mechanism configured to partially block the emitted light, or a diffuser. The control unit may include a dimmer, a light wavelength modifying mechanism or a power switch. In other implementations, the control unit may include a pulsation mechanism configured to automate operation of a power switch. The control unit may also include electrical leads configured to operate the control unit when in contact with an electrically conductive material. The control unit may communicate wirelessly with the light emitter, or via electrical wires.

Disclosed herein are methods of visualizing translucent tissue structures. The methods may include accessing a tissue and positioning a portion of a body of an illumination device behind the tissue. The positioned portion of the body may include at least one light emitter. The method may further include causing light to be emitted from the light emitter and viewing the light through the tissue. The viewed light may reveal properties of the translucent tissue.

In some implementations, accessing the tissue further comprises performing a surgery. The surgery may be a cardiac surgery, or the surgery may be a mitral valve surgery.

In some implementations, positioning a portion of the body may include placing the body adjacent to a valve, a fetus, or an infant, or into a blood vessel or an interior space of an organ. For example, positioning a portion of the body may include placing the portion within a cardiac ventricle, or under a valve annulus. Positioning a portion of the body may include placing an illuminating end of the body behind the tissue.

In some implementations, the body comprises a plurality of body pieces. The body pieces may be curved and elongate. Positioning the portion of the body further may include fastening the plurality of body pieces to each other behind the tissue using at least one coupling mechanism. The coupling mechanism may include one or more of magnets, hook-and-loop fasteners, clips, latches, or bayonet mounts.

In other implementations, the body may include at least one elongate limb. The light emitters may be attached to the limbs, and positioning the portion of the body further comprises positioning the limbs to place the light emitters behind to the tissue. The limb may include at least one malleable adjustment feature. Positioning the limbs may further include adjusting the malleable adjustment feature.

In some implementations, a portion of the body is inflatable. The light emitters may be attached to the inflatable portion, and positioning the portion of the body may include inflating a portion of the body to place the light emitters behind the tissue.

In some implementations, causing light to be emitted comprises activating a chemiluminescent material.

In other implementations, causing light to be emitted comprises generating power from a power source and providing the power to the light emitters. The emitters may include an LED, an electroluminescent wire, or a solid state laser. The power source may be located adjacent the portion of the body that is positioned behind the tissue. Other implementations include avoiding placing the power source behind the tissue.

Some implementations include optical fibers that are optically coupled to one or more light emitters. Causing light to be emitted includes directing light through the optical fiber and emitting it from the light emitter.

In some implementations, the method of visualizing translucent tissues includes controlling the viewed light with a control unit. Viewed light may be controlled by dimming, pulsing, changing a wavelength, or partially blocking the viewed light. In some implementations, controlling the viewed light may include emitting light only when at least one electrical lead contacts a tissue.

The properties of the translucent tissue revealed by the viewed light may include tissue type, tissue transition locations, thicknesses, internal structures, or underlying structures.

Some implementations of the methods include retrieving the light emitter from behind the tissue. The retrieval mechanism may be at least one of a suture, a catheter, or a wire. In other implementations, the retrieval mechanism may be a stick with an adhesive tip. The tip may include a magnetic material designed to adhere to a magnetic material on the body of the device. Alternatively, it may include hook-and-loop fasteners designed to adhere to hook-and-loop fasteners on the body of the device. These implementations may include pulling the retrieval mechanism to retrieve the light emitter.

DETAILED DESCRIPTION

Figure 1A:
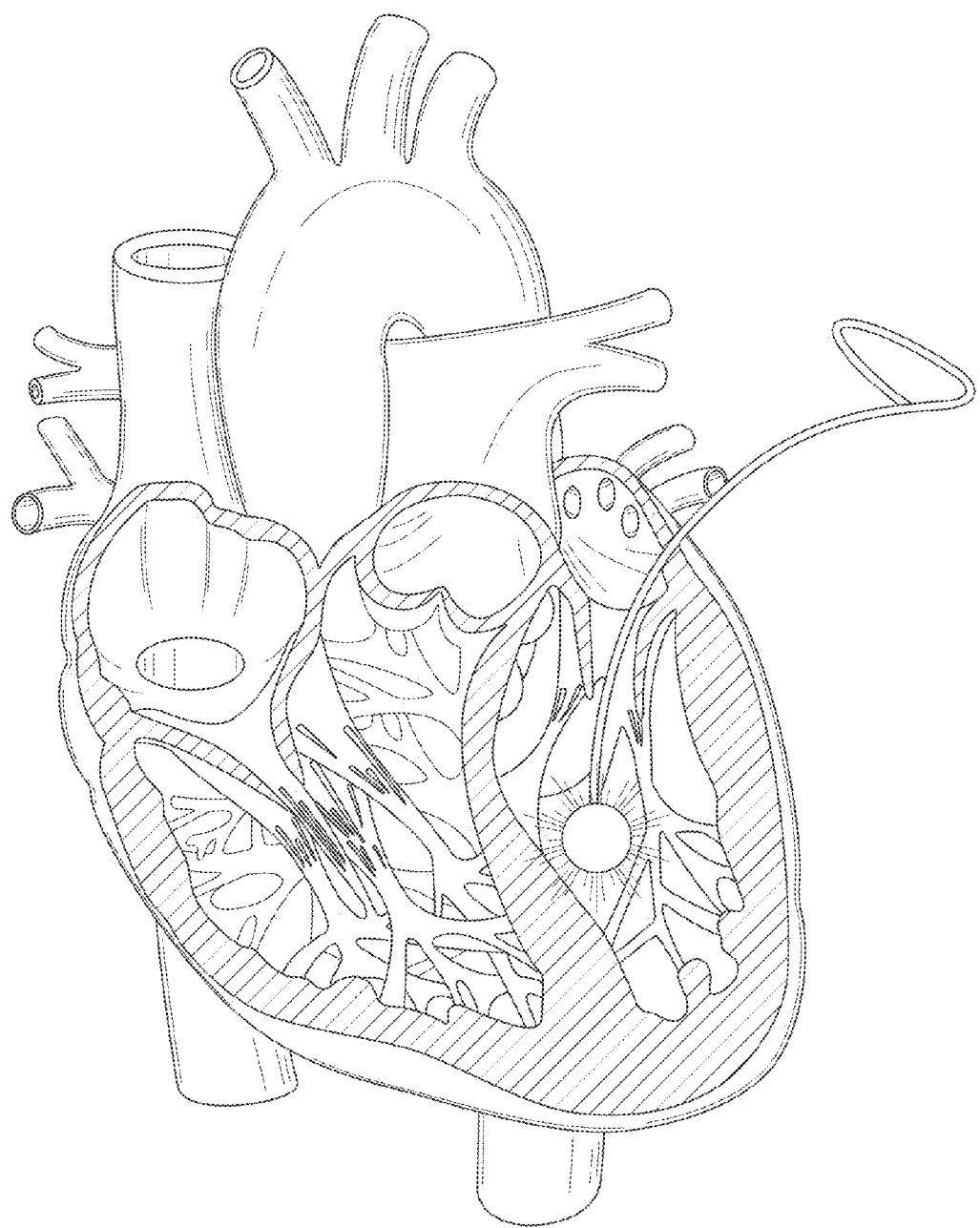
FIG. 1A is a schematic of a light ball implementation of the illumination device, positioned within a cardiac chamber.

Implementations of the systems, devices, and methods disclosed herein take advantage of the translucent nature of tissue to reveal properties by light transmission, for example, tissue type, tissue transition locations, underlying structures, and the like, that are not easily distinguished by reflected light. For example, viewing from a left atrium an annulus and or leaflets of a mitral valve illuminated by a source disposed in a left ventricle reveals additional structure that is difficult or impossible to discern under overhead or front-side illumination. The systems, devices, and methods are described in the context of back-side illumination of a mitral valve from a left ventricle, but are also applicable any suitable application involving surgery on or near translucent tissue, for example, other valves, blood vessels, organs with ducts or lumens, procedures in utero, and/or on infants. Some implementations are applicable to laparoscopic and/or arthroscopic procedures.

Implementations of the devices include at least one light emitter that suitable for placement within a patient, for example, light emitters and/or sources that do not generate excessive heat, dangerous radiation, a dangerous risk of electrical shock, and the like. Examples of suitable light emitters include light sources, for example, light emitting diodes (LEDs), electroluminescent wire, and solid state lasers. Another example of a suitable light emitter is an optical fiber or waveguide optically coupled with a suitable light source.

Some implementations of the light emitters require a power source to generate power for the light emitters. In some implementations, the power source and light emitter are integrated and positioned adjacent each other in or on the device or a portion thereof. In these implementations, the power source is intended and dimensioned for placement within the body of the patient. In other implementations, the power source is not intended or configured for placement within a patient.

Implementations of any of the devices described herein comprise one or more chemiluminescent sources of any suitable type. Examples of suitable chemiluminescent sources generate light using a reaction between hydrogen peroxide and a bisphenol oxalate diester, for example, diphenyl oxalate, di(2,4,6-trichlorophenyl) oxalate, and the like. Some implementations further comprise one or more dyes, which modify the color of the emitted light. Chemiluminescent sources are self-contained, requiring no power source. As such, implementations of lighting devices using chemiluminescent sources are portable and reliable. Some implementations comprising a chemiluminescent source further comprise another type of light emitter or source.

Some implementations comprise an optional control unit, which is operable to modify or control an output of the at least one light emitter. For example, controlling the viewed light may include controlling whether a particular emitter is on or off, or may include controlling the intensity, color, wavelength, duration, or shading of the light. For example, some tissue is more easily visualized or distinguished under certain wavelengths. Pulsation or short bursts of light are useful in some visualizations of the eye to prevent accommodation of the user's iris. Some implementations of the control unit include a wired connection to the at least one emitter, while other implementations use a wireless connection. Some implementations of the control unit, such as diffusers or shields, shade or partially block the emitted light. Some implementations of the control unit may include a dimmer to adjust the light intensity. In some implementations including a plurality of emitters, a property of at least a first emitter, for example, intensity and/or color, is adjustable relative to at least a second emitter.

Left Ventricular Ball Light

Figure 1B:
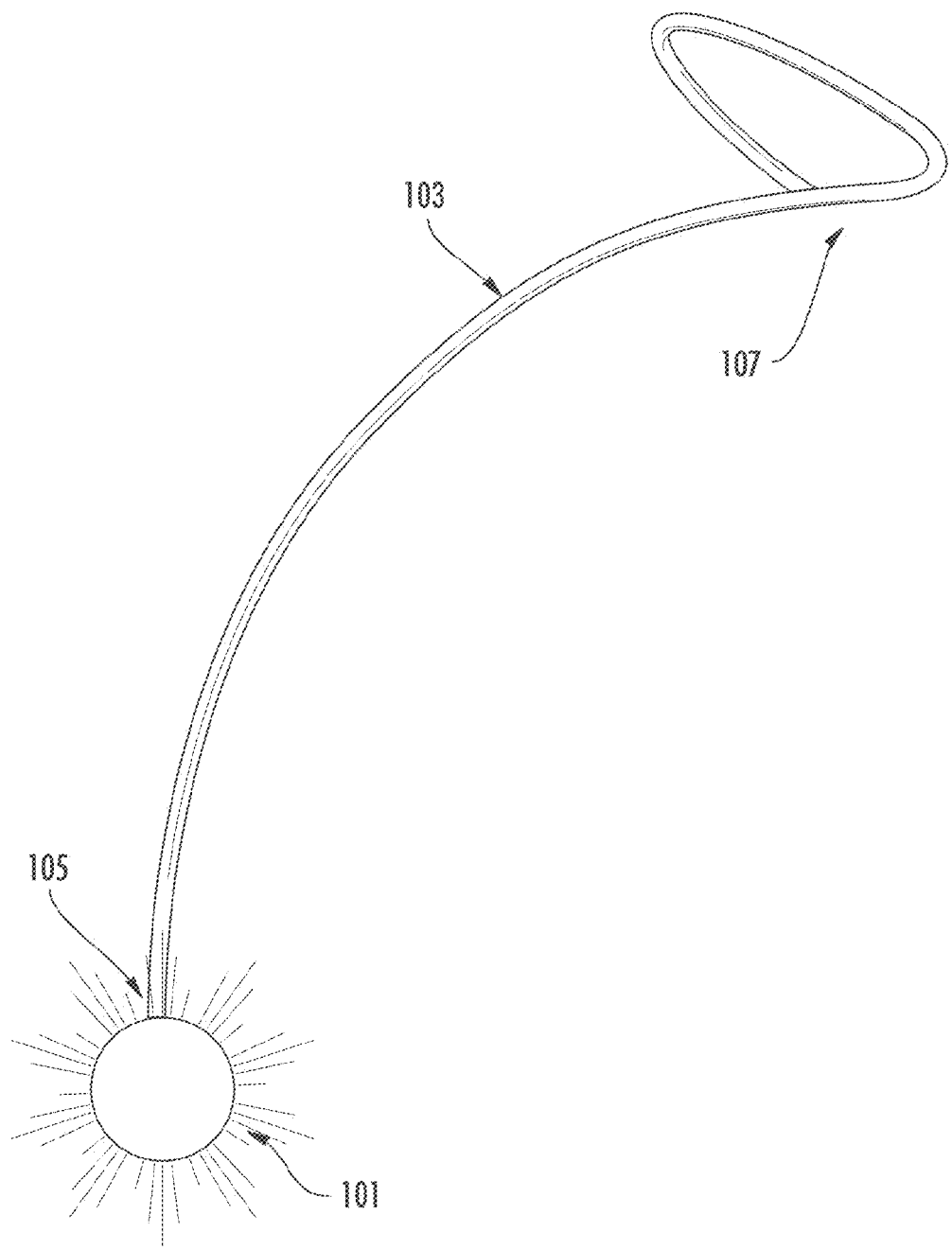
FIG. 1B is a schematic of the light ball from FIG. 1A.

Some implementations of the illumination device are dimensioned for placement within the left ventricle with the output of the one or more light emitters directed outwards. For example, the light may be directed towards the annulus of the mitral valve. FIG. 1A schematically illustrates an implementation of a ball light positioned within a cardiac chamber. Ball light implementations may be a self-contained device comprising a power source and a source of light in the shape of a ball. Other implementations comprise an external power source, and optionally, a control unit. FIG. 1B illustrates an implementation of the illumination device with a body in the shape of a ball 101. In this example, the light emitters are one or more LEDs supported by and integrated into the body 101. In some implementations, the device is deployed at the beginning of the procedure and retrieved post repair or replacement. In other implementations, the device is deployed and/or retrieved at different times, for example, deployed for improved visualization at a certain step or set of steps in a procedure. Some implementations of the illumination device include a positioning mechanism 103. The positioning mechanism may comprise a permanent suture with a first end 105 attached to the device and a second end 107 external to the patient. The second end 107 may be a loop of a suture line. In some implementations, the positioning mechanism may comprise hook-and-loop fasteners, retrieval sticks, magnets, or any other system that would permit easy deployment and retrieval. In some implementations, the positioning mechanism comprises a flexible and/or malleable rod or other elongate member.

Figure 1C:
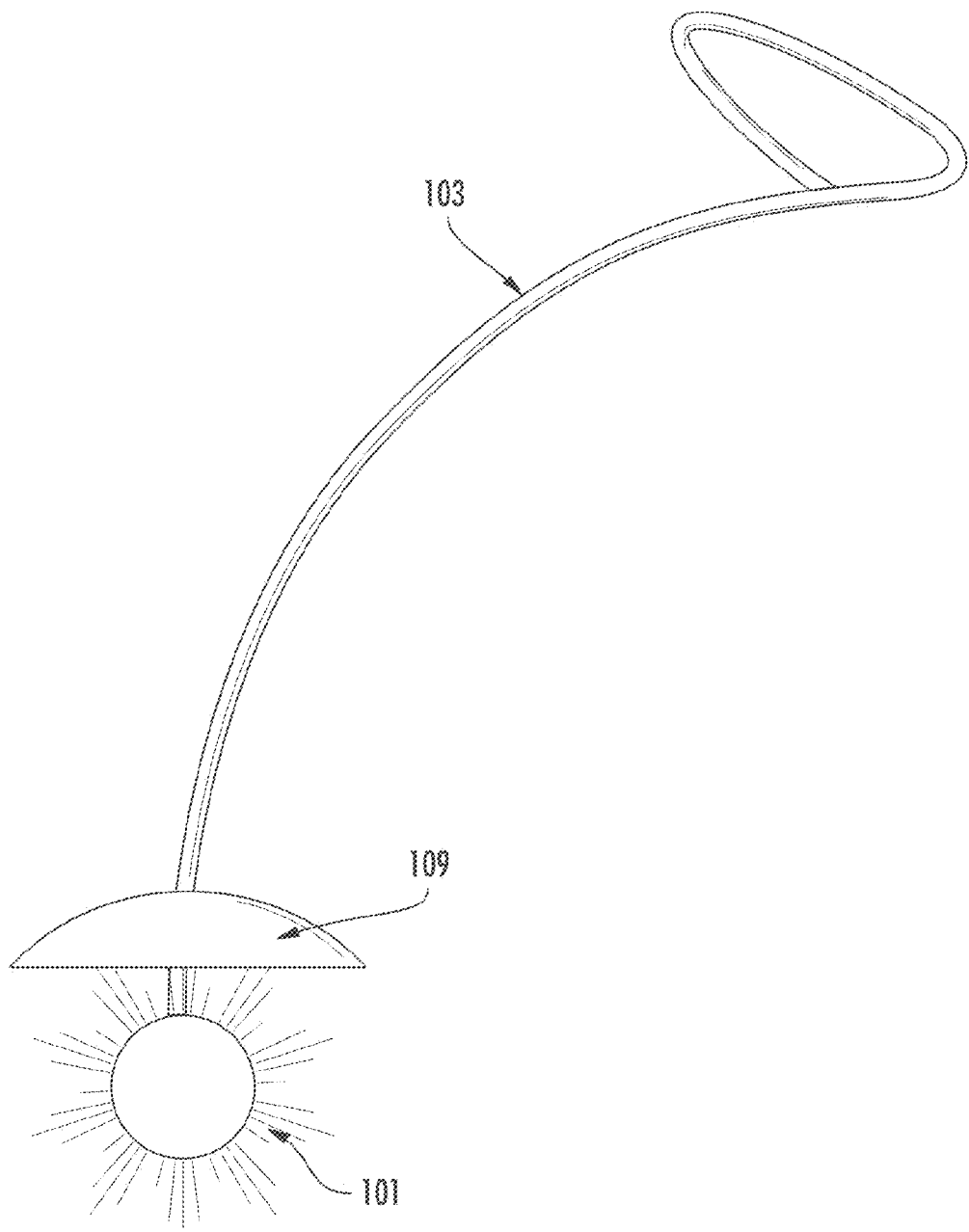
FIG. 1C illustrates an implementation of a light ball with a shading mechanism.
Figure 1D:
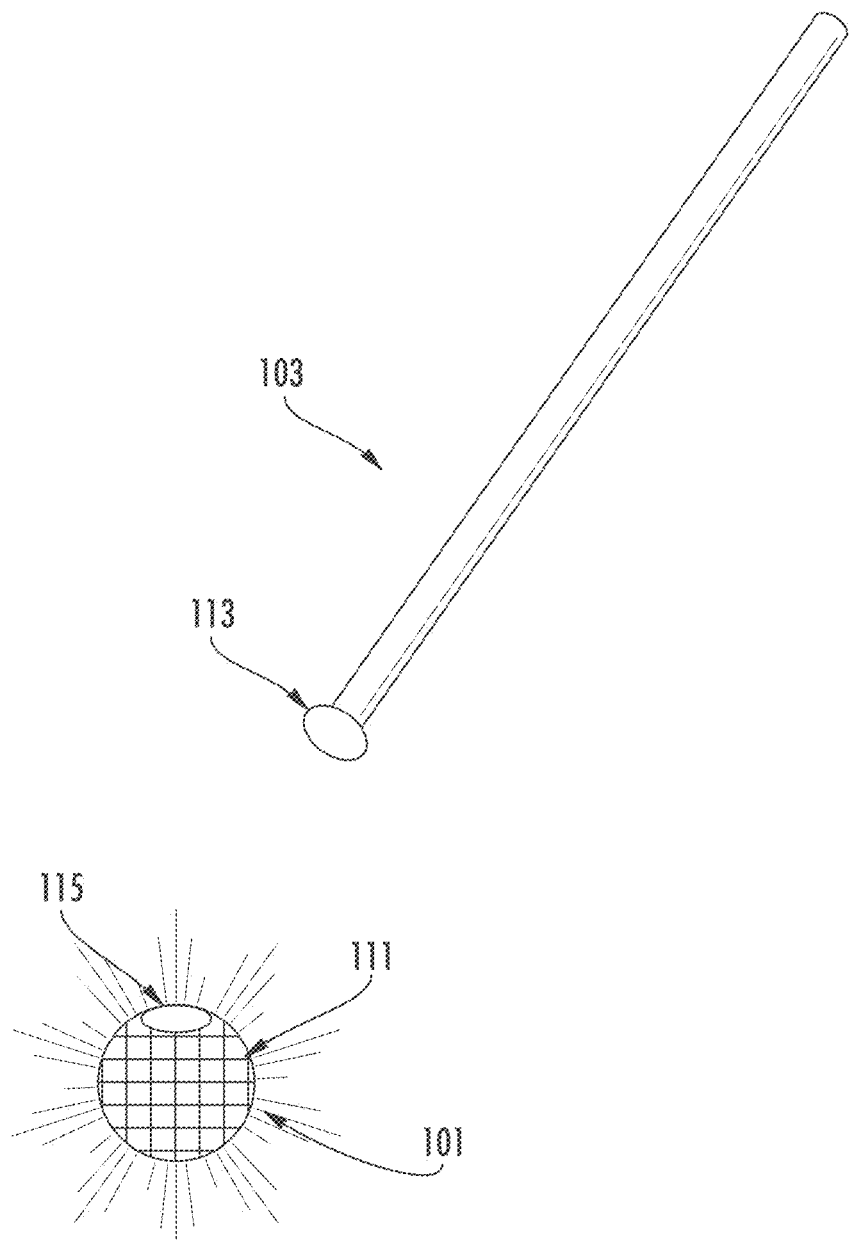
FIG. 1D illustrates another implementation of a light ball with a shading mechanism and a retrieval stick.

As illustrated in FIGS. 1C-1D, some implementations may include a shading mechanism configured to partially block the emitted light. The implementation illustrated in FIG. 1C includes an optional, adjustable shield 109. The shield may block or redirect light, for example, away from a surgeon's eyes. In some implementations, a tint of the shield 109 is electronically controllable, either for the entire shield or independently for different portions or sections thereof. In some implementations, the shield in incorporated into the device 101 itself, for example, at or near a surface thereof. The implementation illustrated in FIG. 1D includes a diffuser 111 that permits sufficient light to shine through the tissue, but not so much as to overwhelm the user during a surgical procedure, as well as to even out the light intensity to provide a more accurate impression of relative tissue thickness, type, and/or color. In some implementations, an intensity of the one or more light sources is adjustable, either globally, or for individual light sources in the device. For example, an externally placed control unit may include a dimmer to adjust the light intensity.

The implementation illustrated in FIG. 1D illustrates an alternative implementation of the positioning mechanism 103. The positioning mechanism 103 is a retrieval stick with an adhesive tip 113. In this implementation, the adhesive tip is designed to adhere to the body of the illumination device. For example, in FIG. 1D, the tip 113 is magnetic and adheres to a magnetic portion 115 on the body of the light ball implementation.

Light Rope

Figure 2A:
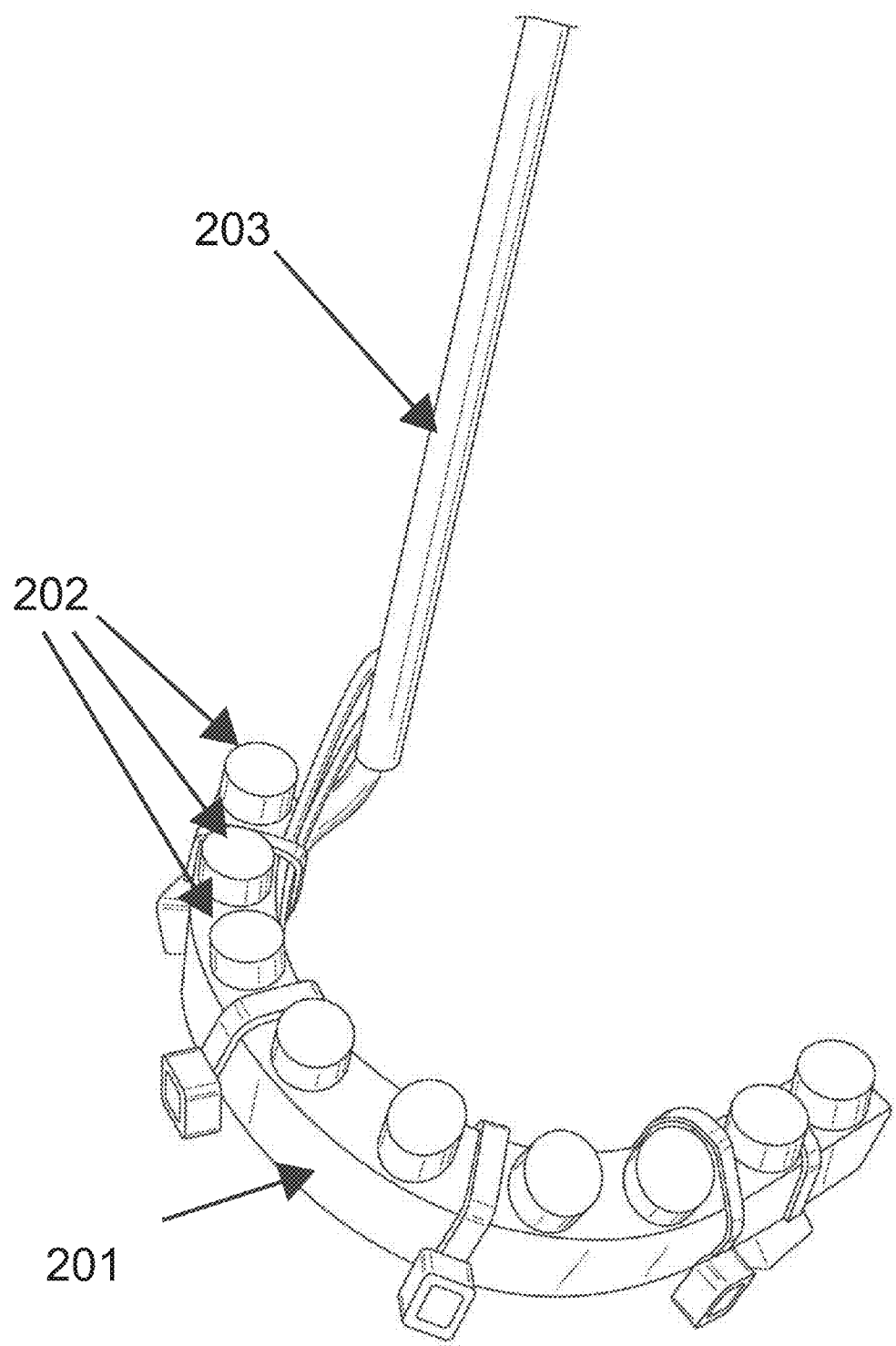
FIG. 2A illustrates a light rope implementation of the illumination device.
Figure 2B:
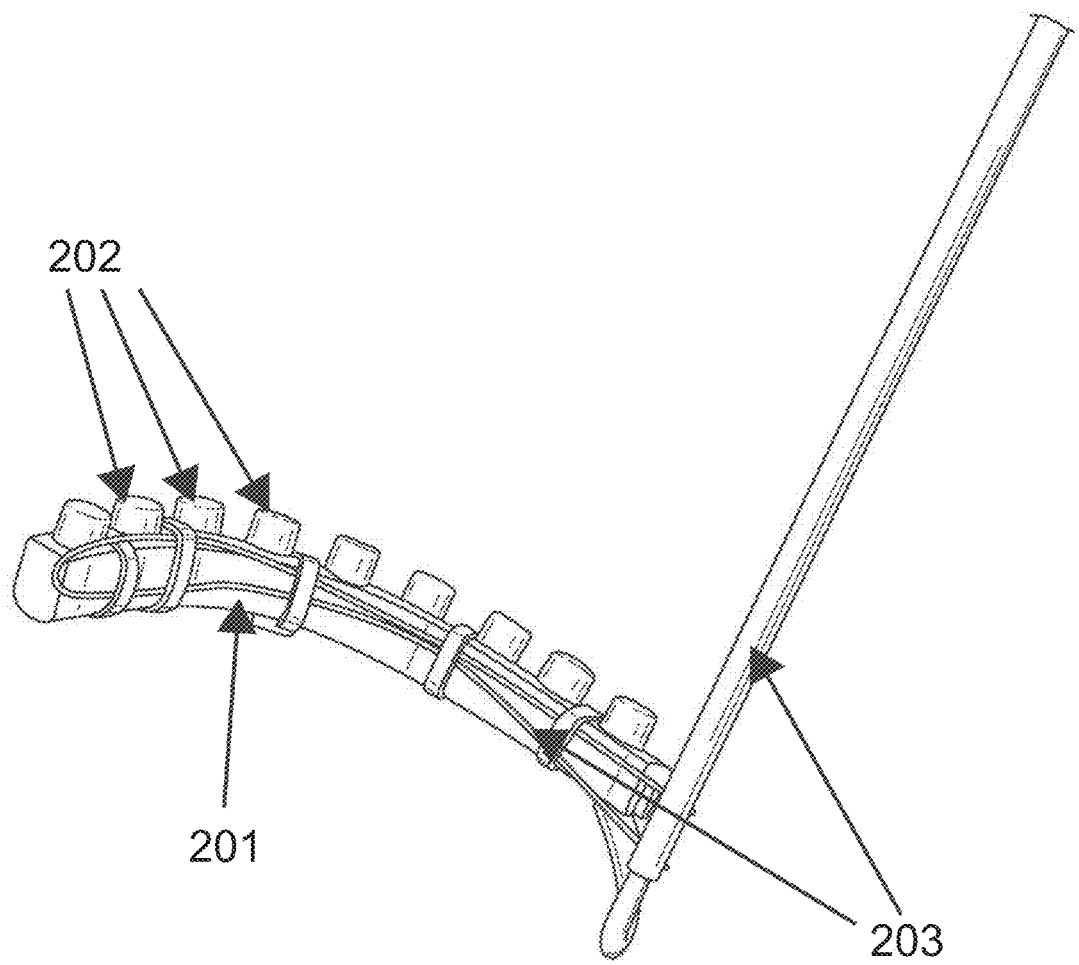
FIG. 2B illustrates another view of the light rope implementation of FIG. 2A.
Figure 2C:
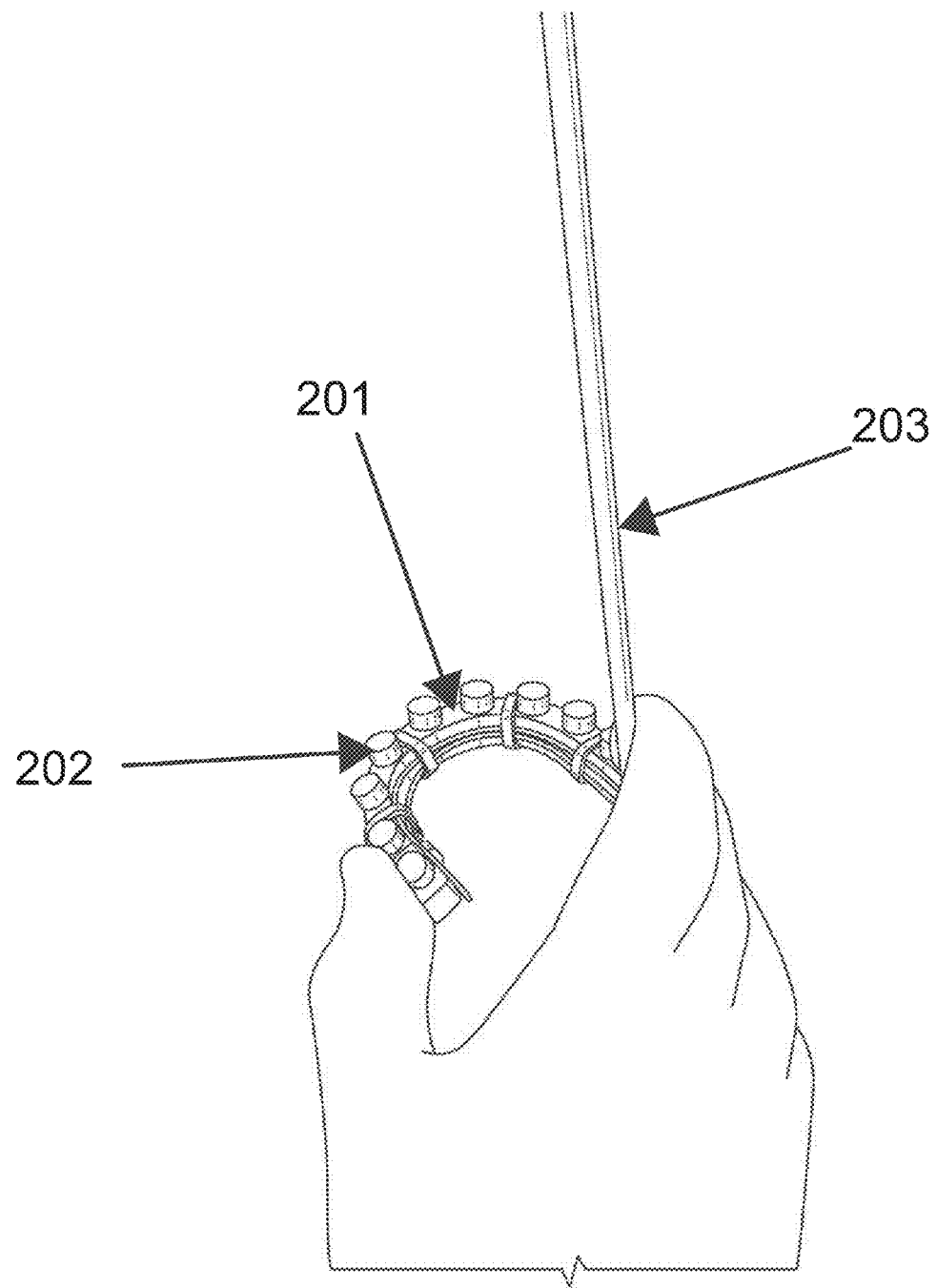
FIG. 2C illustrates another view of the light rope implementation of FIG. 2A.
Figure 2D:
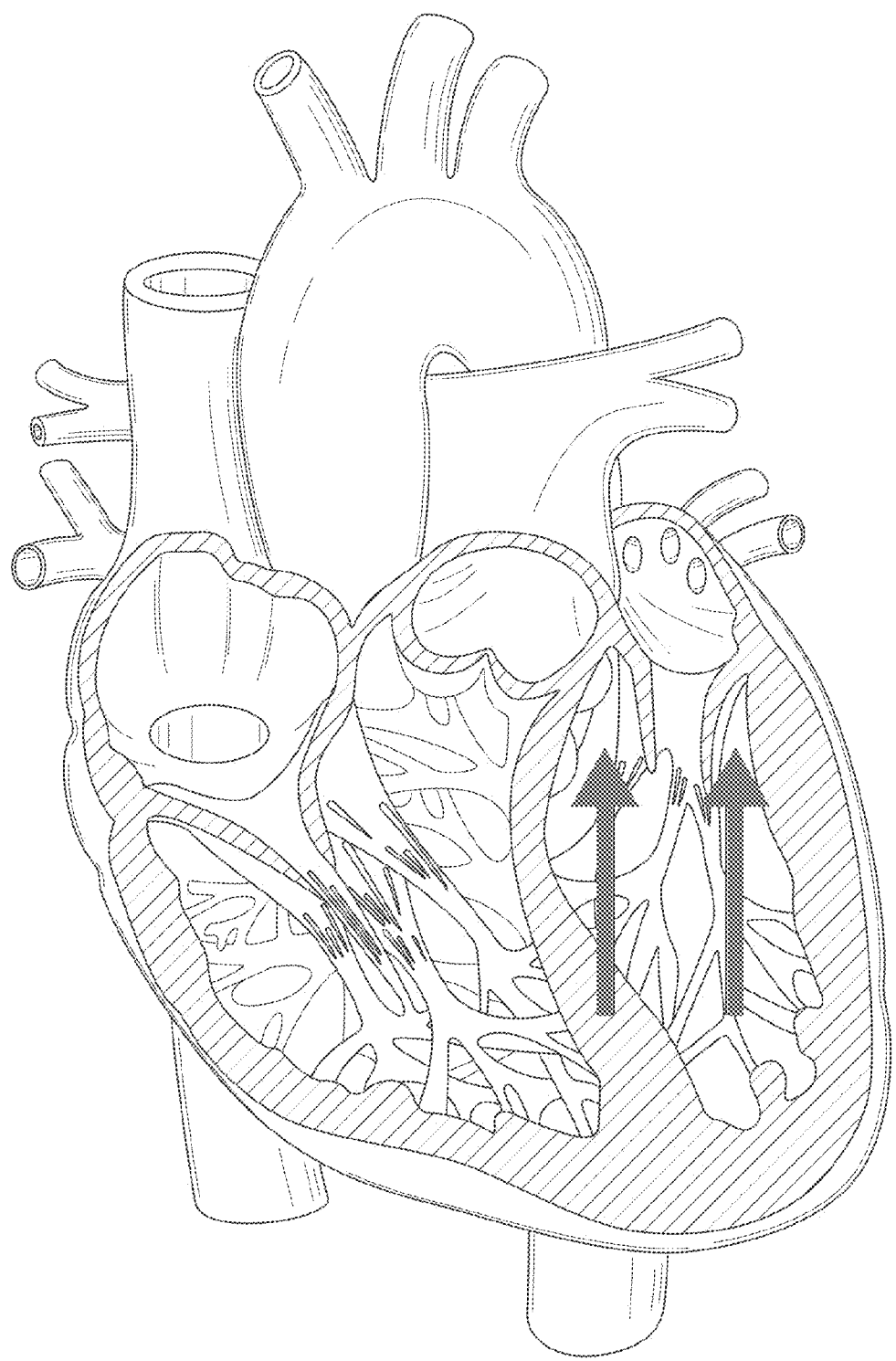
FIG. 2D demonstrates a location in which the implementation of FIG. 2A may be positioned during operation.

As illustrated in FIGS. 2A-2C, some implementations of the illumination device include a light rope with a flexible, elongate body 201 and an external power source. The body of the light rope supports at least one light emitter 202. The light emitters may include an array of LEDs, at least one electroluminescent (EL) wire, or another source of compact, localized light. In some implementations, the illumination portion comprises fiber optic light emitters optically coupled to an external light source. A positioning device 203 may be used to thread the body and light emitters through a mitral valve commissure, around chordae tendineae, and position them snugly around and under the valve annulus (in the location shown by the arrows in FIG. 2D).

Figure 2E:
FIG. 2E is a photograph of a cardiac valve when a light rope implementation is positioned and in operation. The valve leaflets are pulled taut in this image.
Figure 2F:
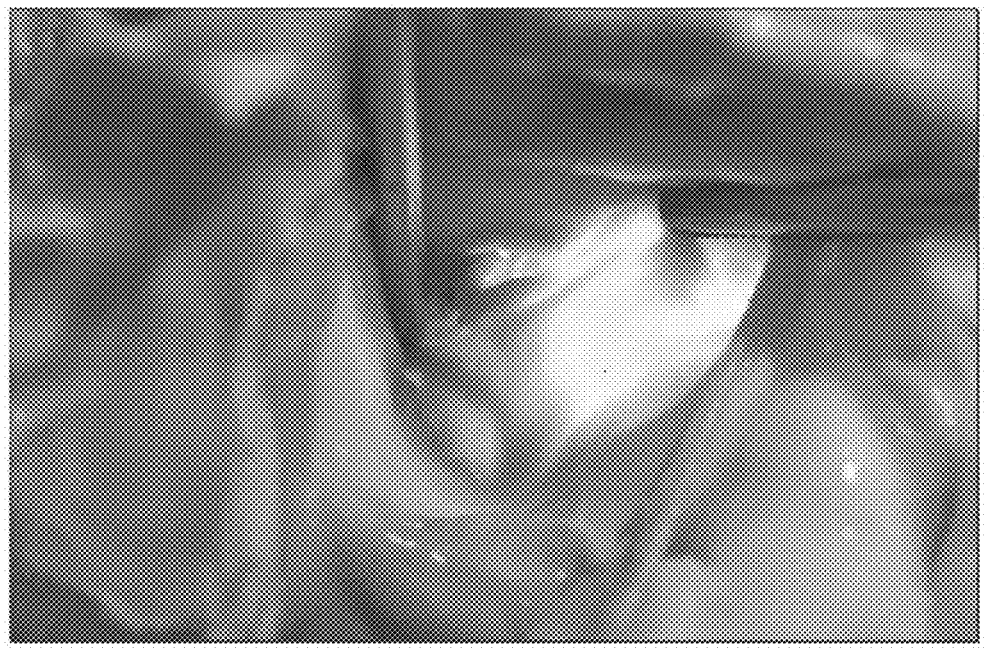
FIG. 2F is another photograph of a cardiac valve when the light rope is positioned and in operation. The valve leaflets are pulled taut in this image.
Figure 2G:
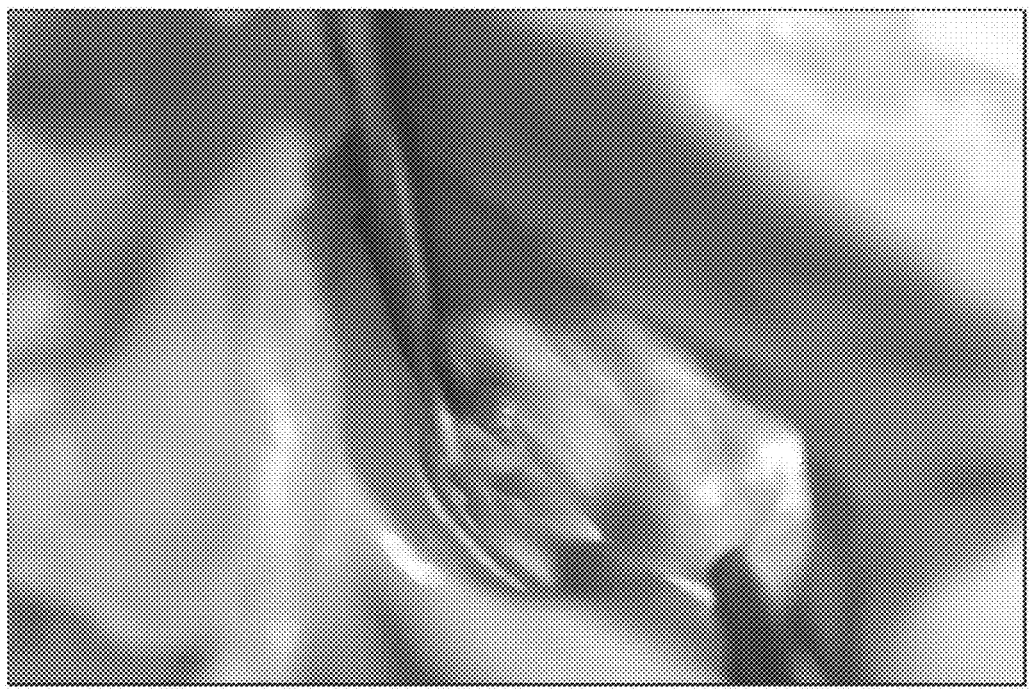
FIG. 2G is another photograph of a cardiac valve when the light rope is positioned and in operation. The valve leaflets are pulled taut in this image.
Figure 2H:
FIG. 2H is a photograph of a cardiac valve when the light rope is positioned and in operation. The valve leaflets are not pulled taut in this image.
Figure 2I:
FIG. 2I is a photograph demonstrating a light rope implementation positioned behind a cardiac valve annulus.
Figure 2J:
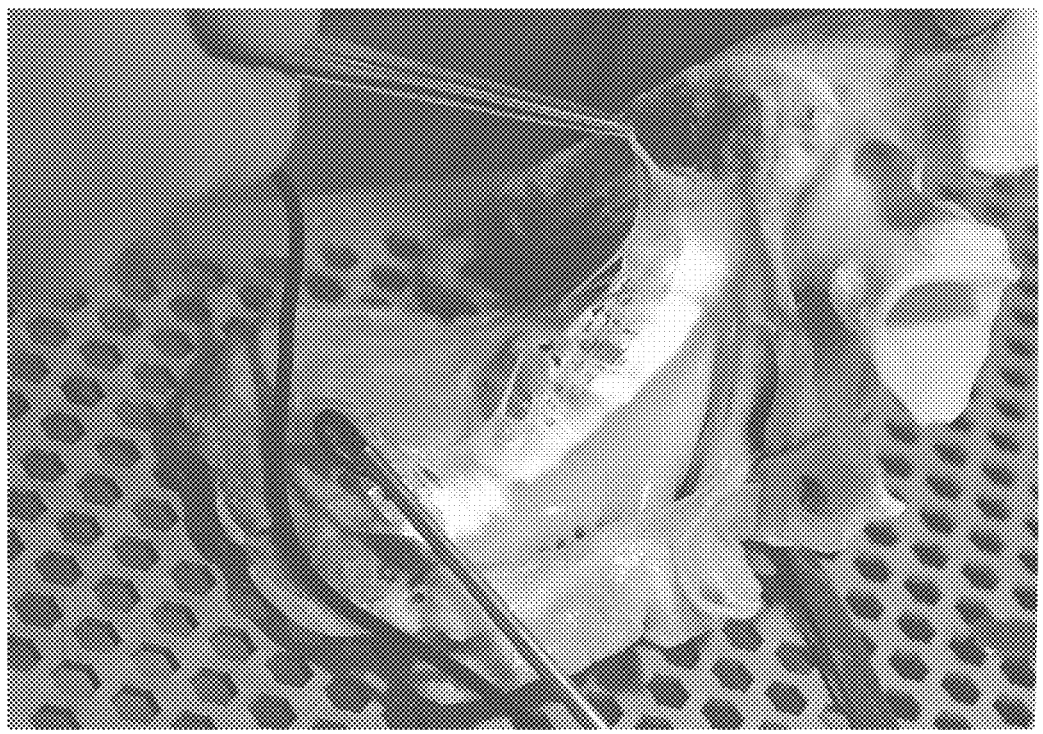
FIG. 2J is another photograph demonstrating a light rope implementation positioned behind a cardiac valve annulus.
Figure 2K:
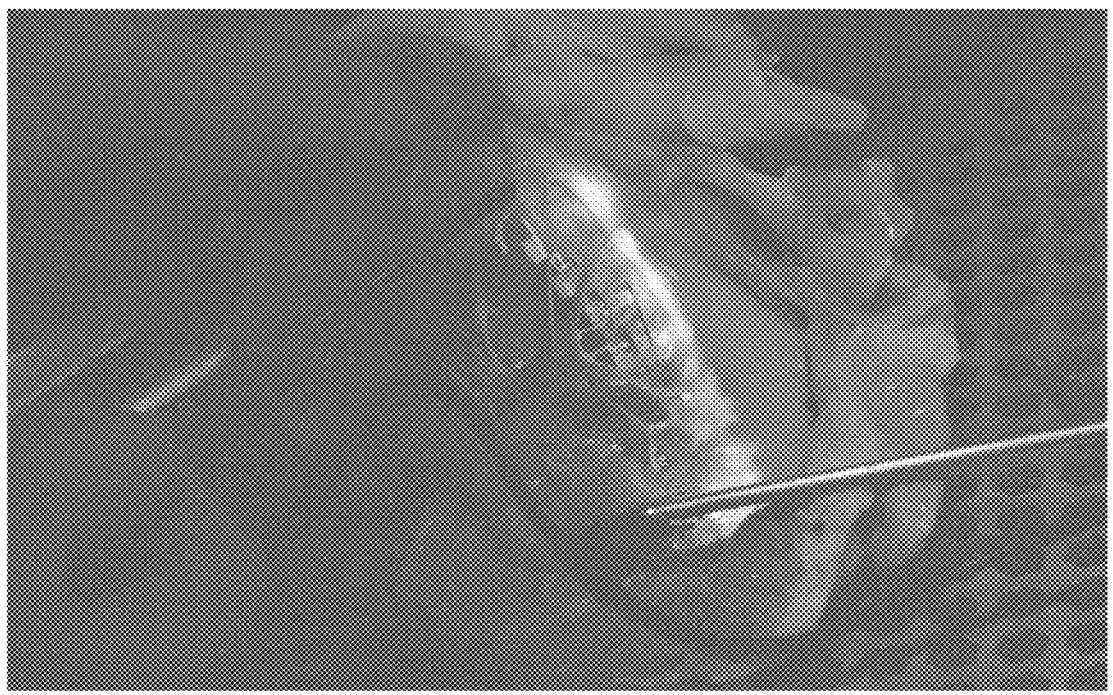
FIG. 2K is another photograph demonstrating a light rope implementation positioned behind a cardiac valve annulus.
Figure 2L:
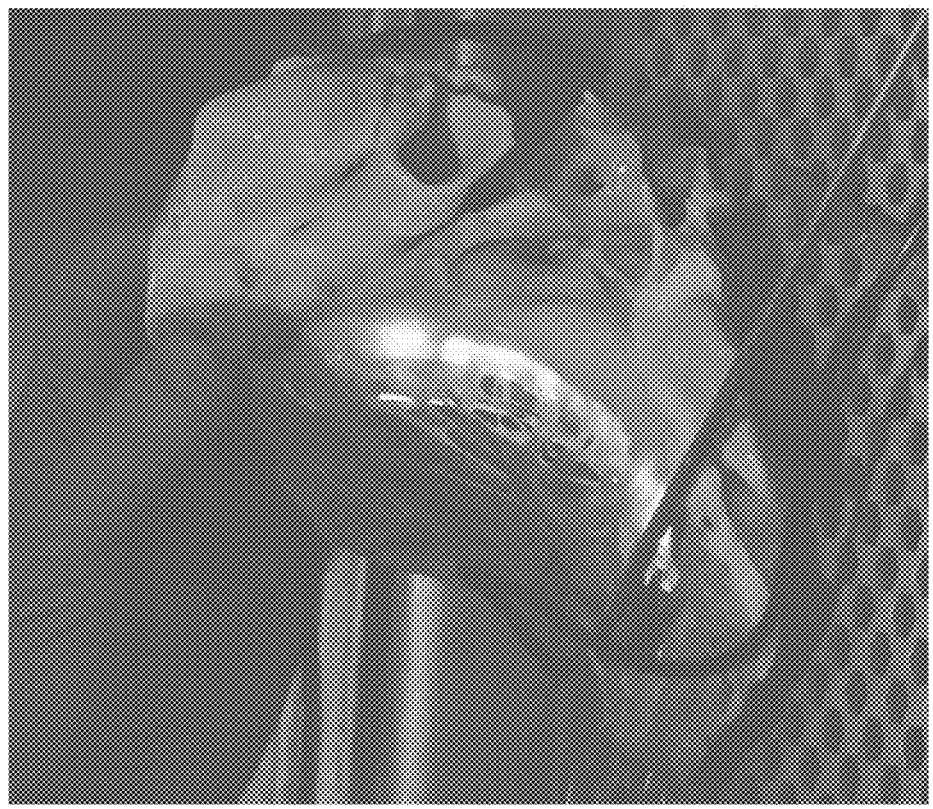
FIG. 2L is another photograph demonstrating a light rope implementation positioned behind a cardiac valve annulus.
Figure 2M:
FIG. 2M is another photograph demonstrating a light rope implementation positioned behind a cardiac valve annulus.
Figure 2N:
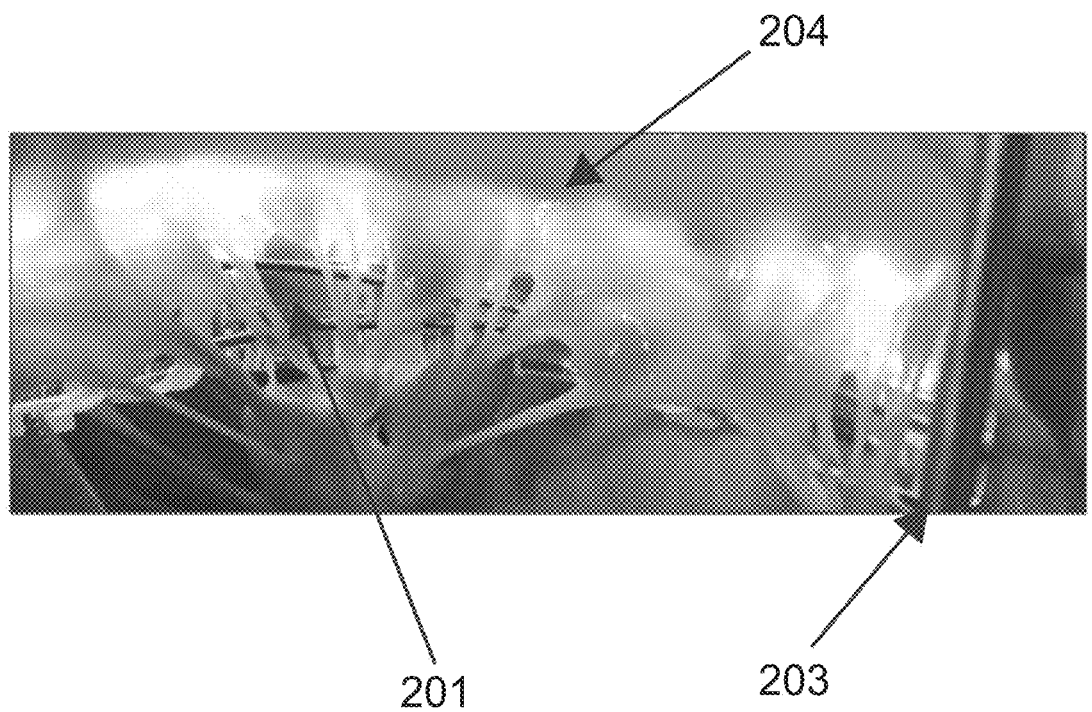
FIG. 2N is a magnified inset of a portion of FIG. 2M.

FIGS. 2E-2G are photographs of the light rope implementation positioned within a cardiac chamber with the cardiac valve leaflets pulled taut. In FIG. 2H, the light rope implementation is positioned within a cardiac chamber and the cardiac valve leaflets are not taut. FIGS. 2I-2L are photographs showing the light rope implementation placed below the annulus of the mitral valve. FIG. 2M-2N are photographs demonstrating that sub-annular illumination of the mitral valve by the light rope implementation permits visualizing the connection 204 between the leaflet and the valve annulus.

Adjustable, Multiple-Source Light

Figure 3A:
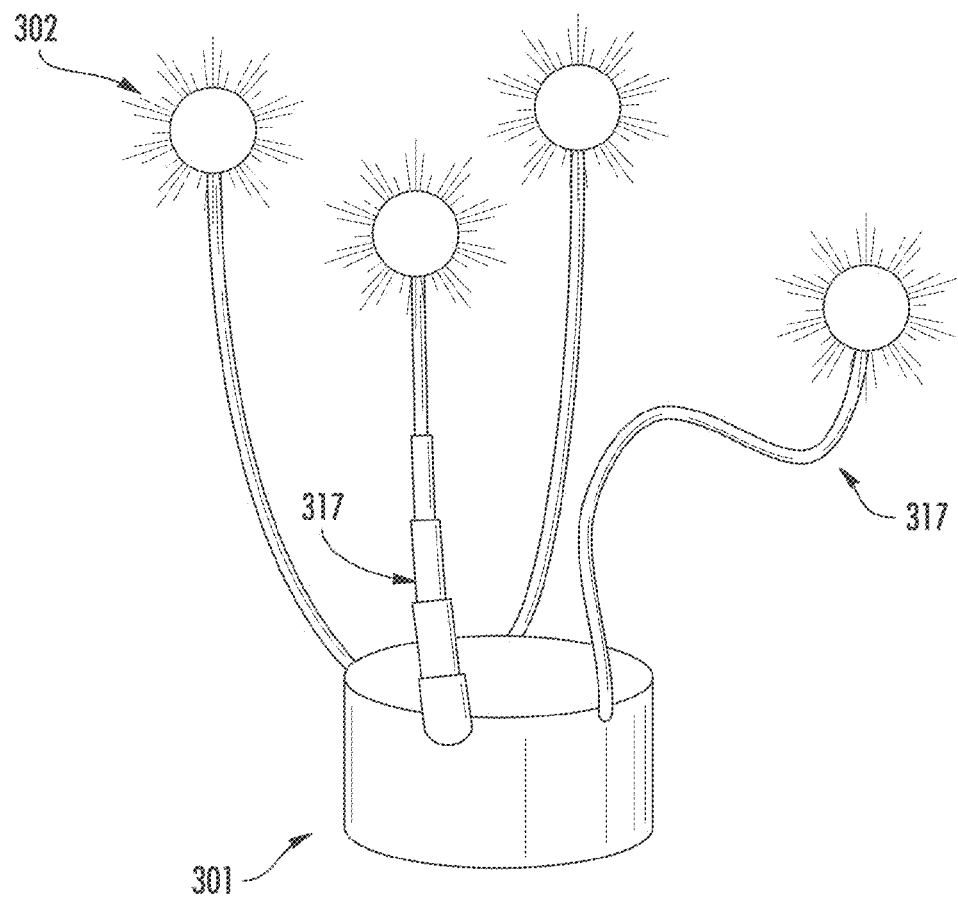
FIG. 3A illustrates a multiple-source light implementation of the illumination device.
Figure 3B:
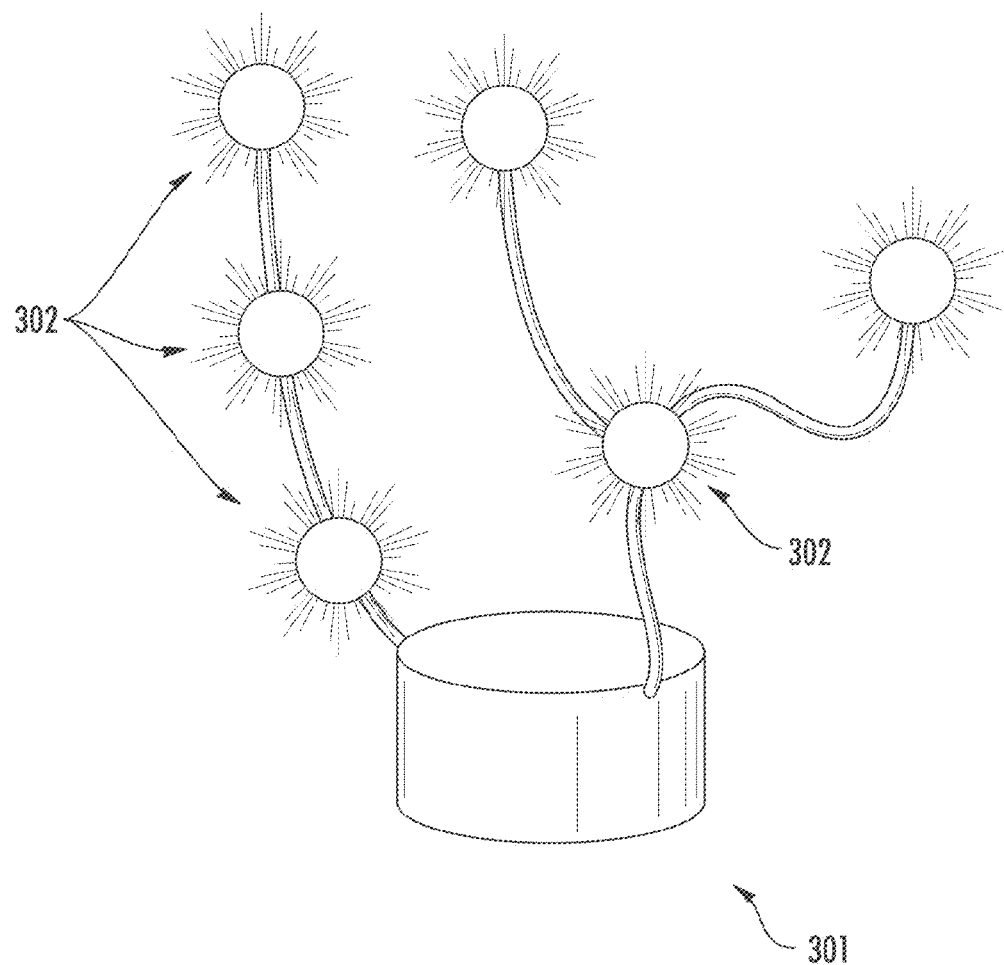
FIG. 3B illustrates another multiple-source light implementation of the illumination device.

FIGS. 3A-3B illustrate implementations of an adjustable, multiple-source light. The adjustable, multiple-source light comprises a body 301 and a plurality of adjustable elongate limbs 317, each terminating in at least one light emitter 302. In the implementation depicted in FIG. 3A, the limbs 317 may include one or more adjustment features, and may be independently adjustable. For example, in some implementations, the adjustment feature may include a malleable material that enables bending and/or twisting, but retains sufficient rigidity to maintain the adjusted shape or configuration. In other implementations, the adjustment feature of at least one of the limbs 317 may include at least one telescoping mechanism, enabling at least one limb is to be telescopically adjustable. In some implementations, the user adjusts the limbs of the device to position the light emitters proximate to desired locations in a patient's anatomy, for example, around the annulus of the mitral valve. In some implementations, like the one illustrated in FIG. 3B, the light emitters 302 are positioned along the length of the limbs, or at branch points between the limbs. Suitable light emitters include LEDs and optical fiber. In some implementations, at least one of the limbs comprises electroluminescent wire.

Balloon Light

Figure 4A:
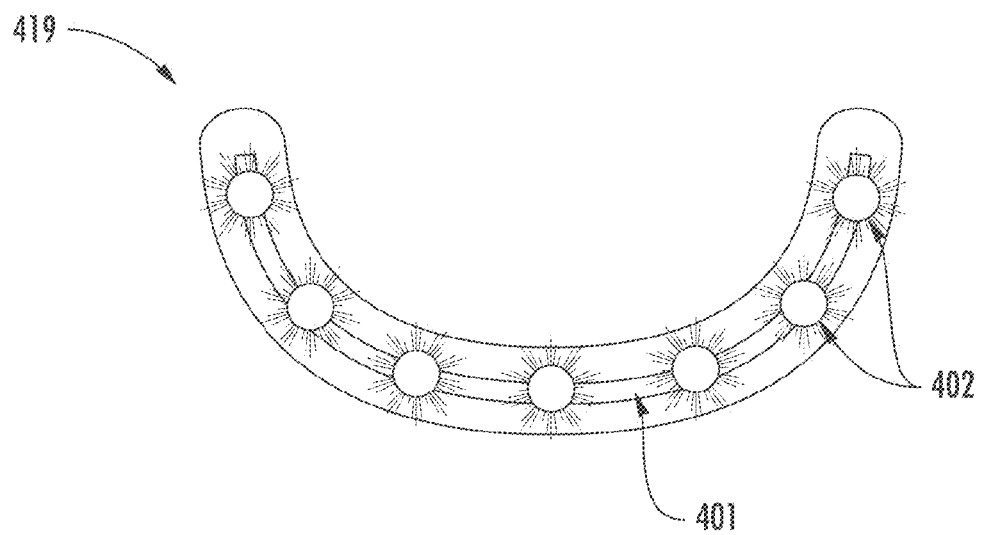
FIG. 4A illustrates an inflatable implementation of the illumination device, in its inflated state.
Figure 4B:
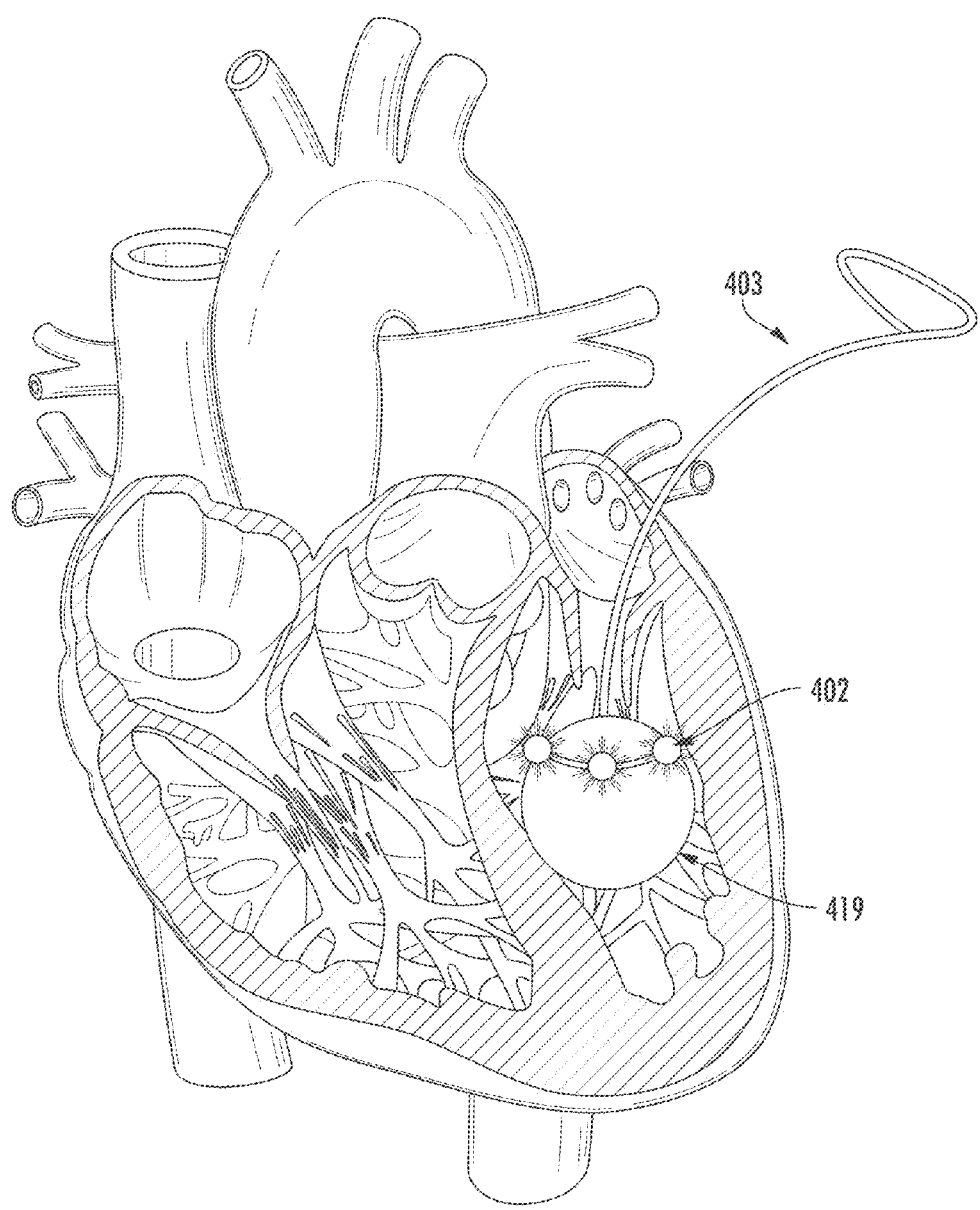
FIG. 4B illustrates another inflatable implementation of the illumination device, in its inflated state and positioned within a cardiac chamber.

FIGS. 4A-4B illustrate a balloon light implementation of the illumination device. The implementation depicted in FIG. 4A includes an elongate, C-shaped body 401 similar to the light rope described above. The body is coupled to a balloon 419. This implementation is dimensioned for disposition in the ventricle along the mitral valve annulus. In the implementation illustrated by FIG. 4A, the light emitters are disposed on an outer surface of the balloon. In other implementations, the light emitters may be disposed within the balloon.

Other implementations of a balloon light, such as the one illustrated in FIG. 4B, comprise a round balloon 419 dimensioned for disposition within the ventricle. Expanding the balloon inflates the ventricle, simulating a filled ventricle, thereby allowing the light emitters 402 to contact and illuminate surrounding tissue. The balloon light implementation of FIG. 4B also includes a positioning mechanism, 403.

Light Catheter

Figure 5A:
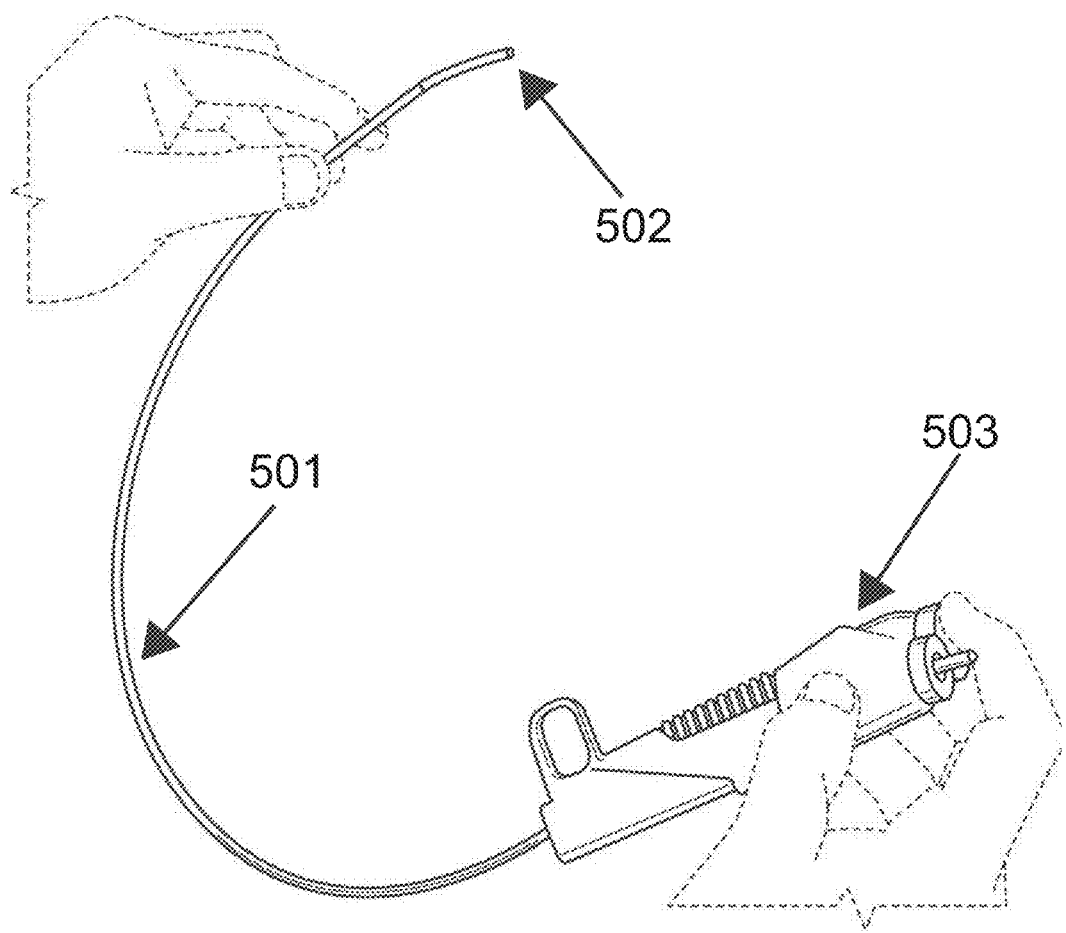
FIG. 5A illustrates a light catheter implementation of the illumination device.
Figure 5B:
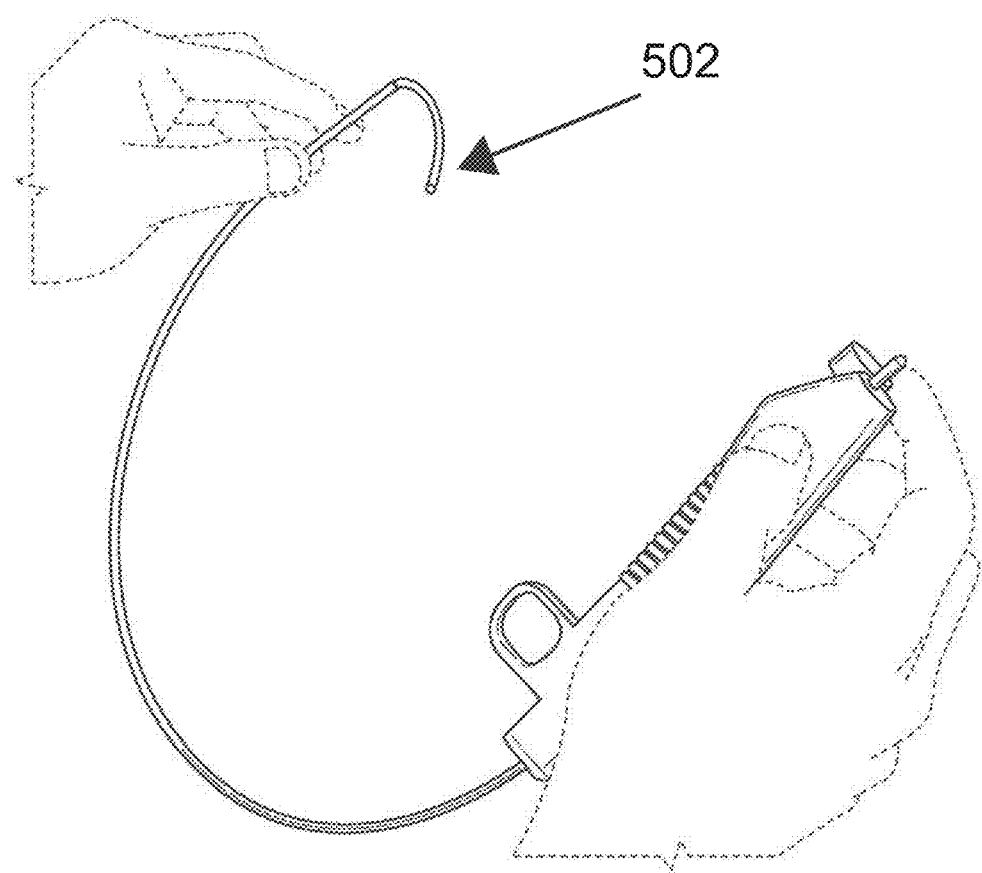
FIG. 5B illustrates another view of the light catheter implementation of the illumination device.

FIGS. 5A-5B schematically illustrates an implementation of a light catheter. Implementations of a light catheter comprise a device similar to a low-profile catheter. The body of the light catheter implementation comprises one or more pre-shaped, bendable, and/or steerable arms 501, on which light emitters 502 are disposed, for example at the distal, illuminating ends thereof. In use, the one or more arms are advanced through the valve and the light emitters positioned or steered into the desired position by the user. The light catheter implementations may include a positioning device 503. For example the implementation shown in FIGS. 5A-5B includes a positioning device in the form of a handle.

Figure 5C:
FIG. 5C is a photograph from the outside of a cardiac valve. The valve is illuminated from behind the tissue by the light catheter implementation of the illumination device.
Figure 5D:
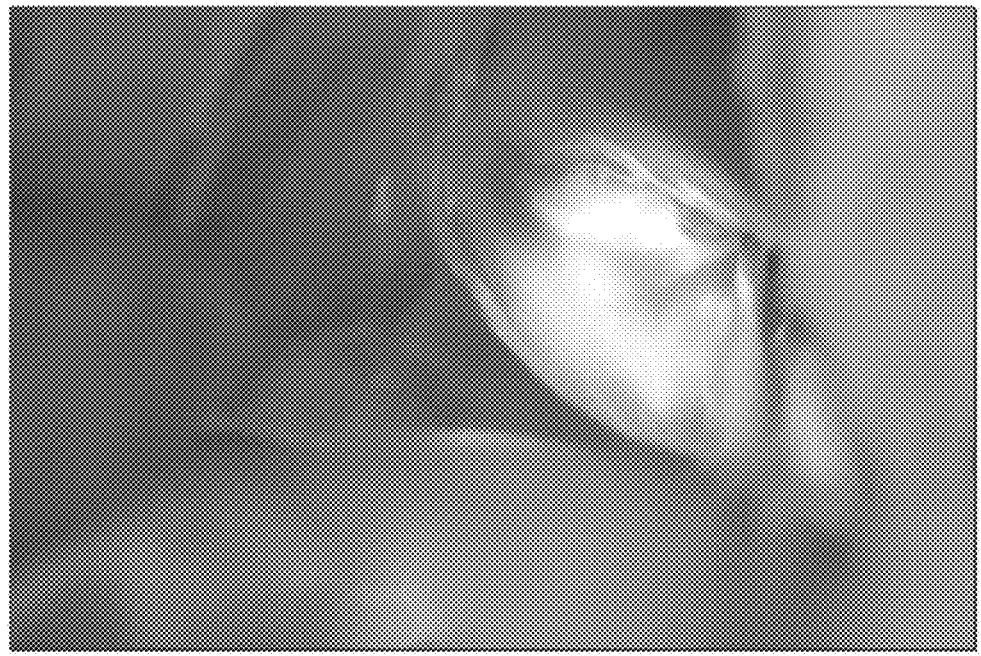
FIG. 5D is a photograph from the outside of a cardiac valve. The valve is illuminated from behind the tissue by the light catheter implementation of the illumination device.
Figure 5E:
FIG. 5E is a photograph from the outside of a cardiac valve. The valve is illuminated from behind the tissue by the light catheter implementation of the illumination device.
Figure 5F:
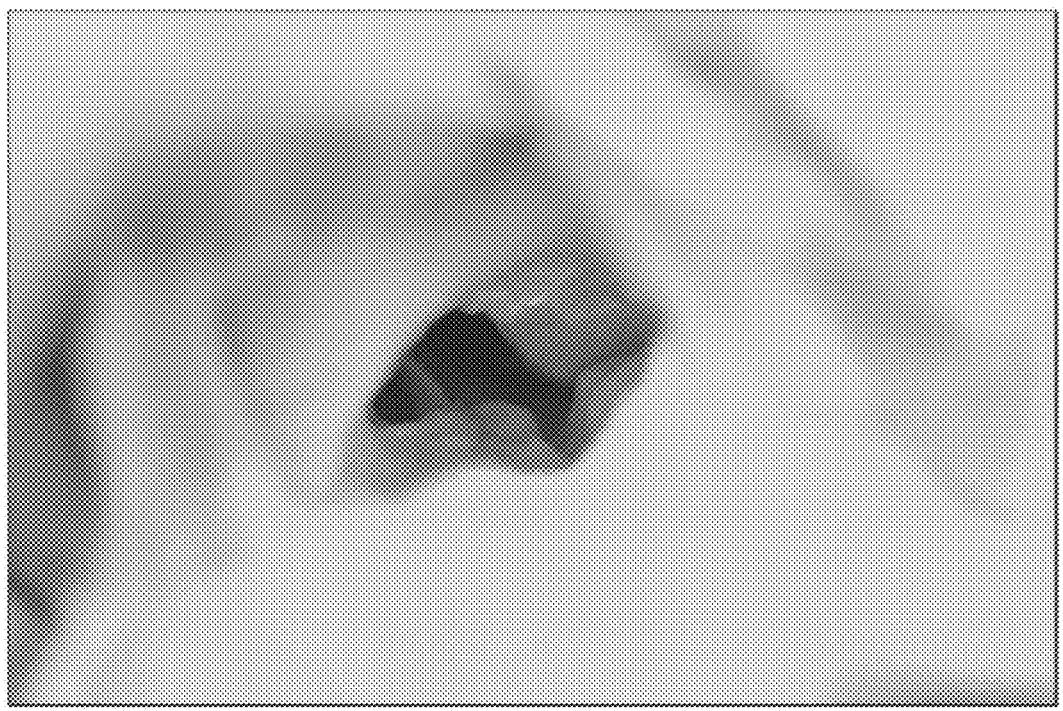
FIG. 5F is a photograph from the outside of a cardiac valve, for comparison to FIGS. 5C-5E. The valve is not illuminated from behind the tissue.

FIGS. 5C-5F are photographs illustrating the use of a light catheter implementation to illuminate a mitral valve. FIGS. 5C-5E depict a mitral valve illuminated by a light catheter implementation from within the cardiac chamber. FIG. 5F shows the mitral valve without illumination from behind the tissue.

C-Light

Figure 6:
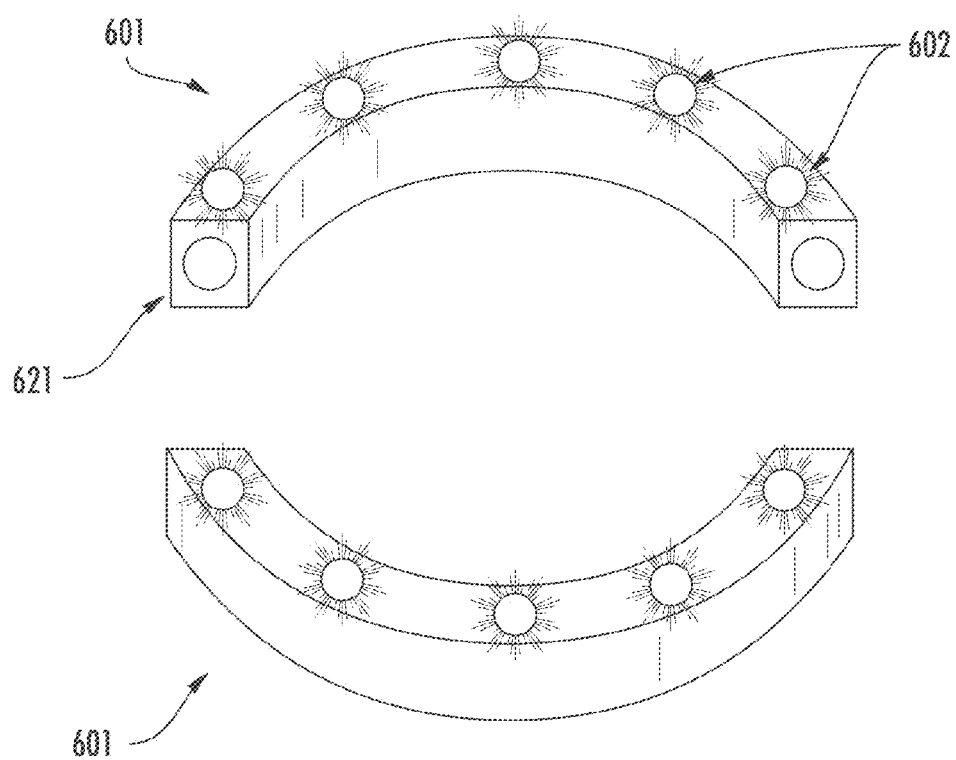
FIG. 6 is an illustration of a C-light implementation of the illumination device.

FIG. 6 schematically illustrates an implementation of a pair of C-lights. C-light implementations may include an elongate array of light emitters 602 disposed on a crescent or C-shape frame or body 601 dimensioned for insertion into the ventricle beneath and extending along the underside of the mitral valve. Some implementations of the C-light include body pieces with ends 621 that are coupleable to other body pieces, thereby illuminating the entire periphery of the mitral valve. Implementations of the ends 621 comprise any suitable coupling means or combination thereof, for example, magnets, hook-and-loop fasteners, clips, latches, bayonet mounts, suture, and the like. In some implementations, the user positions a first C-light body piece within the left ventricle behind the anterior leaflet and associated chordae tendineae, positions a second C-light body piece behind the posterior leaflet and associated chordae tendineae, and couples the proximate ends thereof, securing the assembly beneath the mitral valve and illuminating the tissue thereof.

Forceps Lights

Figure 7:
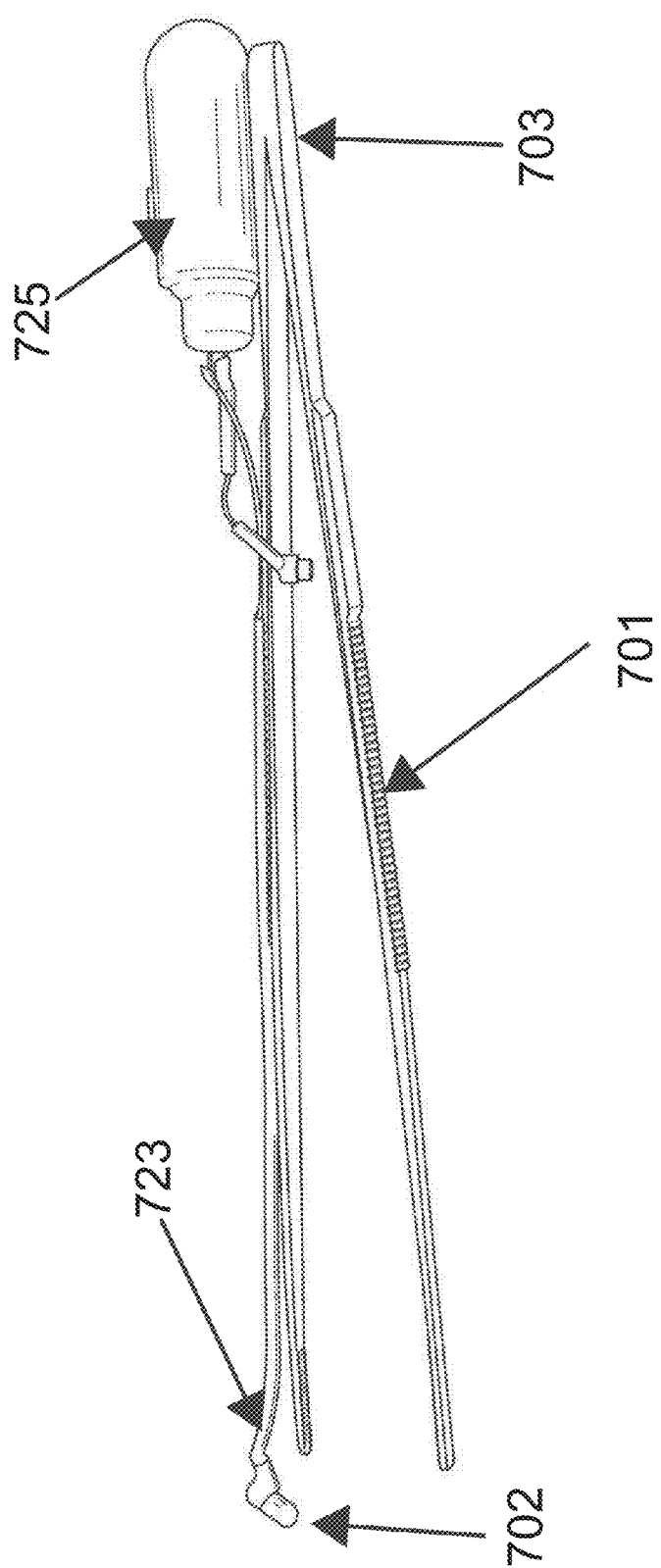
FIG. 7 is an illustration of a forceps light implementation of the illumination device.

FIG. 7 illustrates an implementation of a forceps light. Surgeons use forceps in manipulating structures of the mitral valve and surrounding tissue during a repair and/or replacement procedures. For example, implementations of a forceps light comprise at least one light emitter 702 supported by the body 701 of a pair of forceps, which provides improved illumination of desired locations in the surgical field. The positioning mechanism includes the end 703 opposite the illuminating end. End 703 may be used to control the position of the light emitters. In some implementations, the positioning mechanism includes a flexible positioning member 723 that is permanently or removably coupled to a pair of forceps. The light emitter 702 may be disposed on the flexible positioning member 723. The member 723 is user adjustable to direct and/or modulate the illumination as desired. In some implementations, a power source 725 is also carried on the forceps.

Tissue Contact Leads

Figure 8:
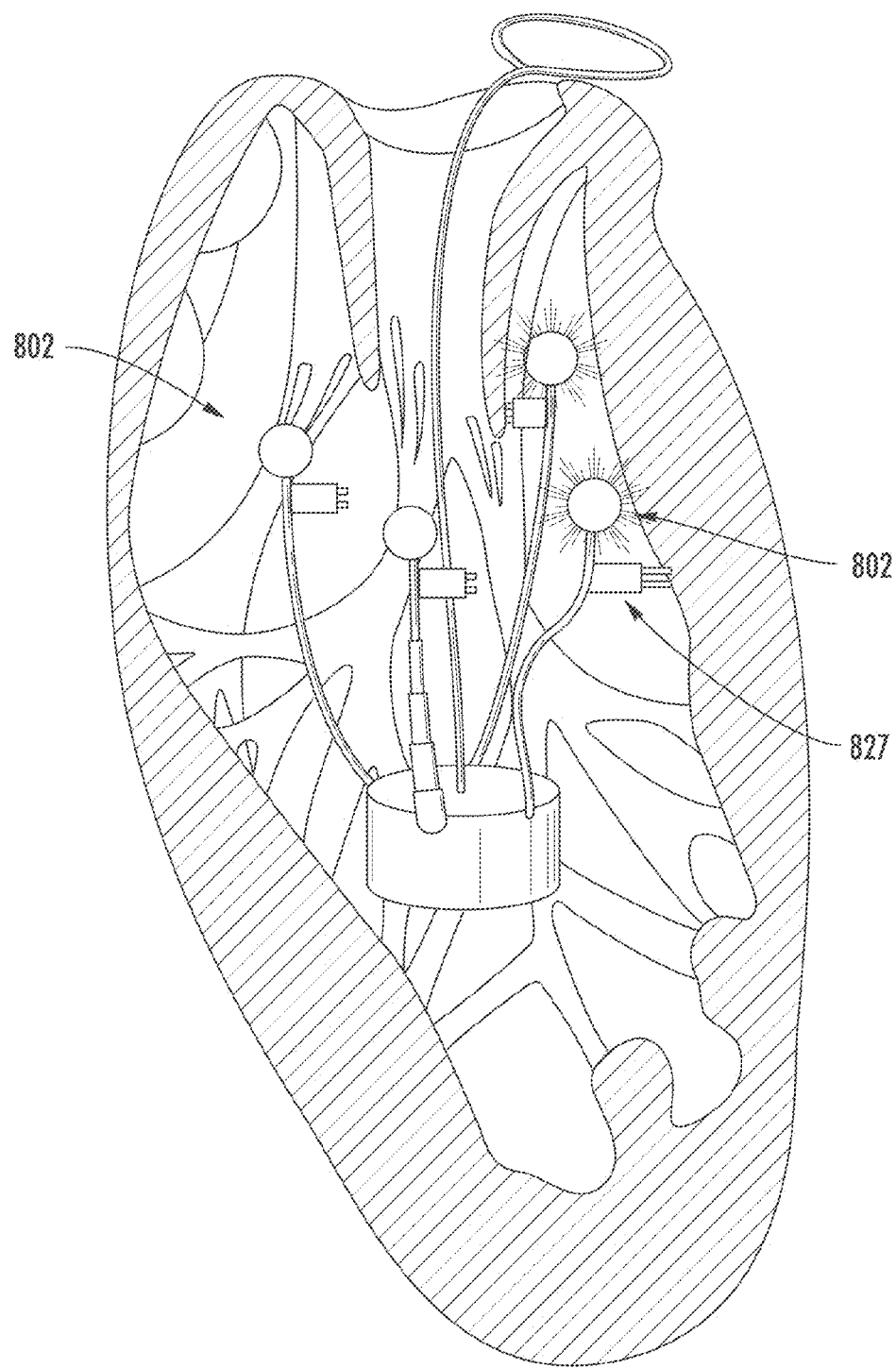
FIG. 8 is an illustration of an implementation of the illumination device similar to FIGS. 3A-3B and including tissue contact leads.

FIG. 8 illustrates an implementation of the illumination device comprising tissue contact leads 827. The lead(s) are disposed at strategic locations on the lighting device such that the one, a plurality, or all of the emitters are activated only when the lead is in contact with tissue. If the lead is not in contact with tissue, the emitter(s) 802 electrically coupled to the lead cannot be activated. The tissue contact leads ensure that the coupled emitter(s) will not be activated unless tissue is interposed between the emitter and the user. In some implementations, the effect of the tissue contact lead can be overridden. FIG. 8 depicts just one implementation including tissue contact leads. In practice, tissue contact leads 827 may be integrated into any of the aforementioned implementations of an illumination device.

In view of the many possible implementations to which the disclosed principles may be applied, it should be recognized that the implementations described and illustrated herein are only examples and should not be taken as limiting the scope of the disclosure

We claim:

1. A method of visualizing translucent tissue structures, the method comprising, accessing a heart valve of a medical patient, positioning a portion of a body of an illumination device under an annulus of the heart valve on a ventricular side of the heart valve's leaflets, wherein the portion of the body positioned under the valve annulus includes a generally arc-shaped structure that carries a plurality of light emitters spaced apart along the arc of the structure, positioning the arc-shaped structure and the light emitters snugly around and under the valve annulus, causing light to be emitted from the light emitters and transmitted through tissue of the heart valve annulus, and viewing the light transmitted through the annulus from an atrial side of the annulus opposite the side of the annulus at which the arc-shaped structure is snugly positioned.

* * * * *